United States Patent [19]

Rogers et al.

[11] Patent Number: 5,006,114
[45] Date of Patent: Apr. 9, 1991

[54] MEDICAL VALVE ASSEMBLY

[76] Inventors: Bobby E. Rogers, 1885 Sienna Canyon Dr., Encinitas, Calif. 92024; Robert L. Zimmer, 11705 Gillette, Overland Park, Kans. 66210

[21] Appl. No.: 512,658

[22] Filed: Apr. 20, 1990

[51] Int. Cl.$^5$ .............................................. A61M 5/178
[52] U.S. Cl. ..................................... 604/167; 604/169
[58] Field of Search ............... 604/167, 186, 202, 169, 604/245, 247, 249, 280, 284, 89

[56] References Cited

U.S. PATENT DOCUMENTS

| 4,063,555 | 12/1977 | Ulinder | 604/247 X |
| 4,496,348 | 1/1985 | Genese et al. | 604/169 |
| 4,917,668 | 4/1990 | Haindl | 604/167 |
| 4,935,010 | 6/1990 | Cox et al. | 604/167 |

Primary Examiner—John D. Yasko
Attorney, Agent, or Firm—Harness, Dickey & Pierce

[57] ABSTRACT

A medical valve assembly is described in which the valve assembly has a female luer lock portion on an inlet end of the device and a male luer lock portion on the outlet portion of the valve. A movable piston seals the inlet portion of the valve from the outlet portion when the piston is in the closed position. When a syringe is attached to the inlet portion of the valve assembly, the piston is displaced in a manner that unseals a fluid channel inlet. This connects the end of the syringe to the fluid channel which is connected, at its outlet end, to a catheter or other device, connected to a patient. Thus, medication can be introduced to, or fluids aspirated from, a patient's bloodstream, without the use of a syringe having a needle. When the syringe is removed from the inlet to the valve assembly, the piston is urged by a biasing means into its original closed position creating a seal between the inlet portion of the valve and the outlet portion of the valve. This feature maintains catheter patency. The top surface of the piston along with the area of the female luer lock connector does not have any fluid reservoir and can be easily cleaned to prevent the possibility of bacterial infection as a result of repeated uses of the valve assembly.

18 Claims, 4 Drawing Sheets

NO FLUID FLOW

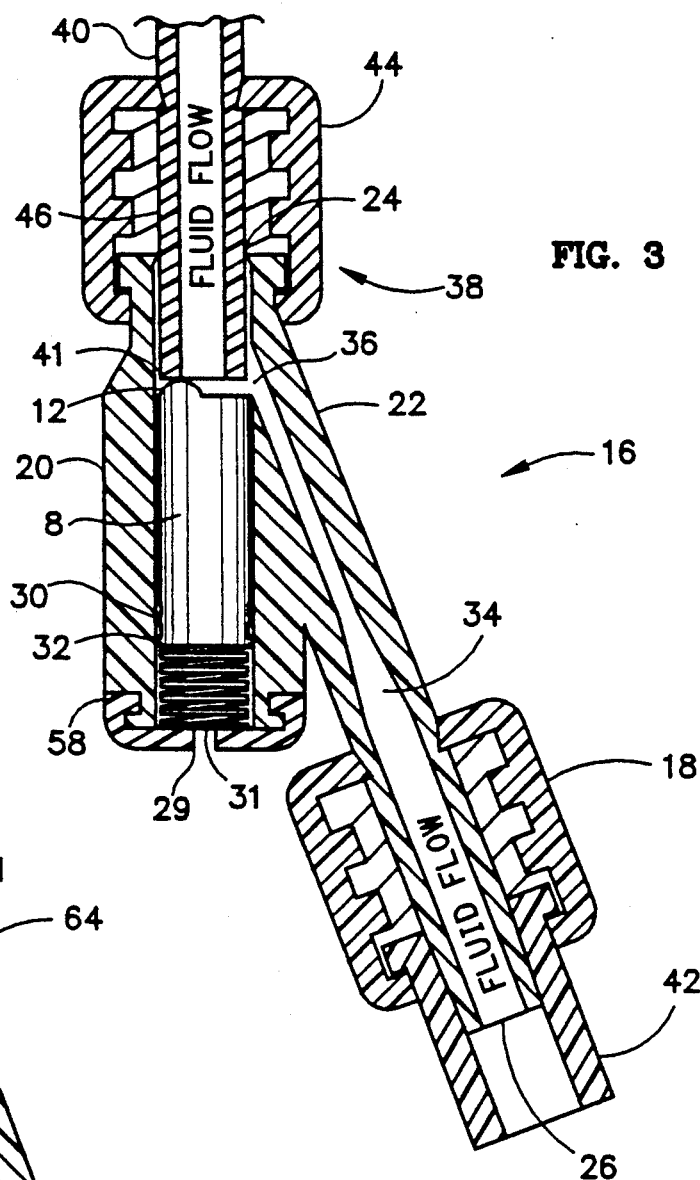
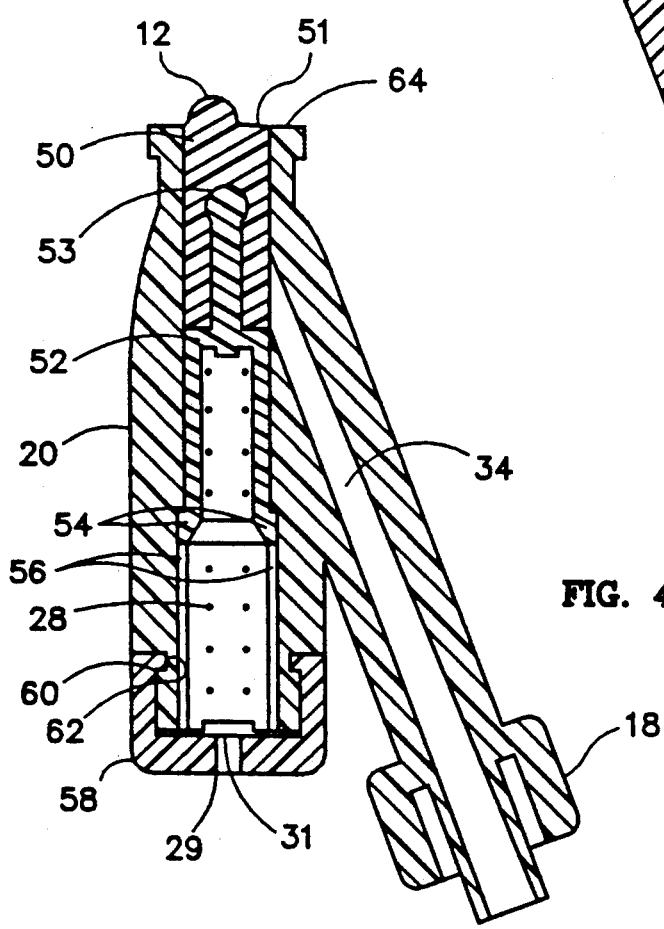
FIG. 3
FIG. 4

MEDICAL VALVE ASSEMBLY

DESCRIPTION

1. Technical Field

This invention relates to medical valve assemblies used in the care and treatment of injured or sick patients. Such valves are used for the purpose of introducing medication into a patient and for aspirating fluids from the patient in a manner that is safe for the patient as well as the person administering the medicine.

2. Background

In current medical practice, it is commonly necessary to deliver various medications or fluids to a patient.

Intravenous (I.V.) therapy is conducted by placing a needle or a plastic cannula (catheter) directly into a patient's vein to deliver fluids and medications. This same process of placing a needle or catheter directly into a patient's vein or artery is used to aspirate fluids.

The conventional practice is to establish a vascular access site as described above and then to introduce medications or aspirate fluids through a secondary needle which is inserted into a sealed entry port. A sealed entry port that is attached directly to a needle or catheter is typically termed a heparin lock. A sealed entry port which is integral to tubing through which fluid flows to and from the needle or catheter is typically called a Y-site.

The sealed entry port of the heparin lock or Y-site is constructed with a latex septum or latex plug. A latex septum is advantageous in that it allows for multiple insertions of needles to access a patient's system with little pain or discomfort to the patient. Upon removal of a needle, the latex septum is self-healing, thus maintaining a closed system. The self healing aspect is very important in that before and after each needle insertion, the latex surface can be wiped down with an alcohol prep pad to disinfect the surface and minimize the possible introduction of bacteria and potential infection to the patient.

The major problem with the conventional practice is the necessary use of the secondary needle. Once a needle has been exposed to a patient's body fluids it is considered high risk and biohazardous to health care workers. Used needles must be handled and disposed of very carefully. The possibility of a health care worker contracting the AIDS virus, Hepatitis B virus, and other bloodborne pathogens as a result of a needle stick injury is well documented and life threatening.

Each needle stick injury results in increased costs, increased anxieties, and a decrease in productivity to both the health care worker and to the hospital. The hospital may bear the cost of blood tests for both the patient and health care worker, the cost for treatment should an infection occur, and the cost of damages associated with the loss of life or the ability to work.

The problem discussed above presents a serious health hazard to health care workers and potentially devastating costs to health care institutions.

Several devices, such as those shown in the U.S. Pat. Nos. 3,570,484 and 4,324,239, show devices that allow access to the patient's bloodstream without the use of a needle. Systems of this type are advantageous in that they eliminate the risk for medical personnel of being stuck by a needle that has been in contact with the patient's body fluid. However, other considerations concern the patient's safety. Any device connected to the patient's blood stream should not have an exposed fluid reservoir due to the potential for bacterial infection from contact with a bacteria contaminated object. If the fluid reservoir or cavity is not cleaned, then there is a potential for developing bacteria in the reservoir. That bacteria could be introduced into the patient's bloodstream when the device is subsequently used to administer new medication or to aspirate fluids from the patient's bloodstream.

Other requirements for such a valve are that it would be inexpensive, disposable, easily manufactured and be adaptable for use in a variety of medical situations including medical emergencies.

The device should have a top surface connection area that is easily cleaned with alcohol and there should be no exposed fluid reservoir that could foster the growth of bacteria. The device should also be easily connectable to a syringe, IV administration sets or other devices using fittings such as a luer fitting and the device should maintain catheter patency when in the closed or sealed position.

Therefore, an object of the present invention is to provide an access valve that does not require the use of a needle to dispense medications to, or aspirate fluids from a patient but utilizes industry standard luer connections.

It is also an object of the present invention to provide a connection device that is easily cleaned and that does not have an exposed fluid reservoir, thus providing a bacterial barrier at least equivalent to current technology which includes heparin locks.

It is a further object of the present invention that such a connection device should maintain catheter patency, be small, inexpensive to manufacture and disposable.

BRIEF SUMMARY OF THE INVENTION

The primary object of the present invention is to provide a valve that is easily connectable to, and provides access to a patient in situations that formally required the use of heparin locks, IV administration or extension sets or any other system where a needle is used to penetrate a self healing membrane for the infusion or aspiration of fluids. To accomplish this, the device has a female luer lock connection on one end of the device. This makes the device easily connectable to a standard syringe, I.V. set, or any other device with a male luer lock or luer slip connection. When a device with such a connection is attached to the present invention, the tip of the male luer connector depresses a silicone oil lubricated piston which is held in place by a biasing means. The piston has a small non-concentrically located bump on the top surface which makes contact with the tip of the male luer connector. During connection the piston is depressed into the open position and the tapered outer sidewall of the male luer connector comes in contact with a sealing lip or an inverse taper which prevents leakage of medication. The bump or raised section on the top of the piston prevents the tip of the syringe from being completely sealed against the top of the piston and thereby allows for fluid flow from the syringe to pass across the top surface of the piston and into a fluid channel, located on the inner diameter of the piston housing, that has been exposed as a result of depressing the piston to the open position. On the other end of the device of the present invention, there is a male luer lock connection which allows fluid flow and easy connection to a catheter, intravenous needle hub or other similar connection point.

When the medication or fluid has been dispensed, the syringe or I.V. set is disconnected from the female luer lock. As this takes place, the biasing means forces the piston up into the closed position which seals the fluid channel. When the piston is in the completely closed position, the top surface of the piston, excluding the bump, is flush with the top surface of the luer connector. This provides a surface that can be easily cleaned and that does not have any areas that could act as an exposed fluid reservoir. An exposed fluid reservoir, that is difficult to clean, may come into contact with a contaminated object If this were to occur, the reservoir would act as a medium for bacterial growth and, thus, a potential source of infectious contamination to the patient. The absence of an exposed fluid reservoir greatly diminishes the possibility that bacteria will form that could be introduced into the patient's bloodstream when the valve is subsequently accessed for the dispensing of additional medication.

The invention will be better understood by referring to the accompanying drawings in which:

BRIEF DESCRIPTION OF THE DRAWINGS

FIG. 3 is a side cut-away view of a variation of the invention showing the piston in the open position with a syringe connected to the input side of the device;

FIG. 4 is a side cut-away view of the preferred embodiment of the invention showing a piston assembly in the closed position;

DESCRIPTION OF THE PREFERRED EMBODIMENT

The device of the present invention has a female luer lock on the input side of a valve and a male luer lock on the patient side of the valve for connection to a catheter or other device. The device of the present invention does not require a needle to administer medication to a patient, is easily cleaned and does not have an exposed fluid reservoir that could become a breeding ground for bacteria. The device is small, economical to manufacture, disposable and easy to use.

Figure 1:
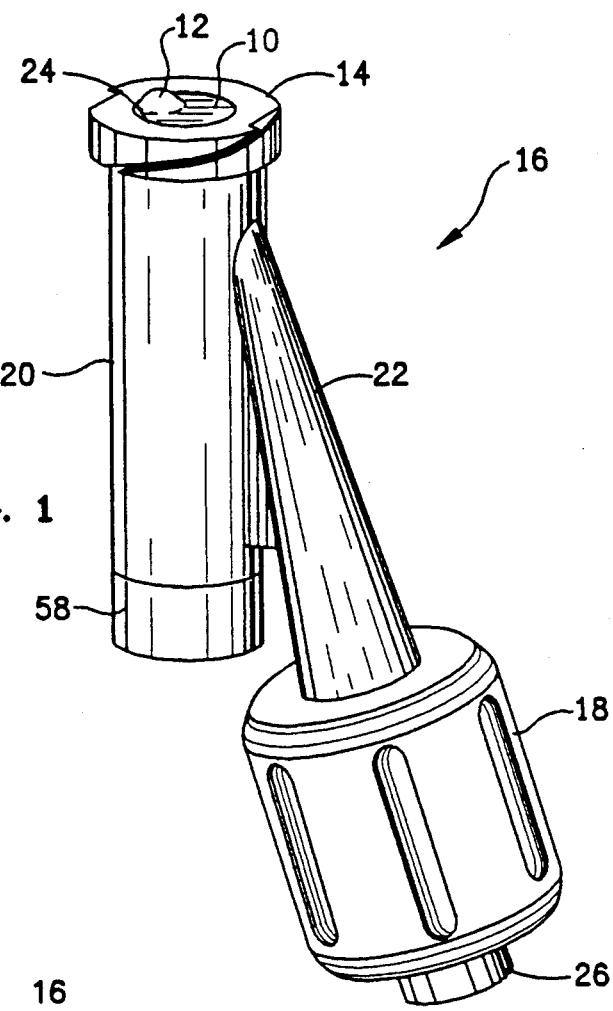
FIG. 1 is a prospective view of the device.

Turning now to FIG. 1, FIG. 1 shows a prospective view of the device of the present invention. The inlet side of the medical valve assembly 16 has a female luer lock portion 14, a piston with top surface area 10 and raised surface area 12, an annular sealing lip 24, a piston and biasing means housing 20, a fluid channel housing 22, a male luer lock connection 18, a fluid outlet 26, and a retaining cap 58. The female luer lock 14 is a standard luer connection. On an interior portion of this luer lock connection is located a piston that has a flat surface area 10 and a raised portion or bump 12. The relationship of flat surface are 10 and raised bump 12 are further shown in FIGS. 2 and 3. The piston extends down into the center portion of piston and biasing means housing 20. In FIG. 1, the piston is shown in the closed position.

At a point approximately ¼ inch below the top surface of female luer lock connector 14 is a fluid channel with an inlet portion which is adjacent to the body of the piston when the piston is in the closed position. This inlet portion of the fluid channel is shown in FIGS. 2 and 3, which will be discussed below.

The fluid channel extends through the bottom portion of the medical valve assembly 16 and terminates at a male luer lock 18. The fluid exits through the fluid outlet 26. From that point the fluid can enter a catheter attached to a patient. Further aspects of this invention will now be discussed with reference to FIG. 2.

Figure 2:
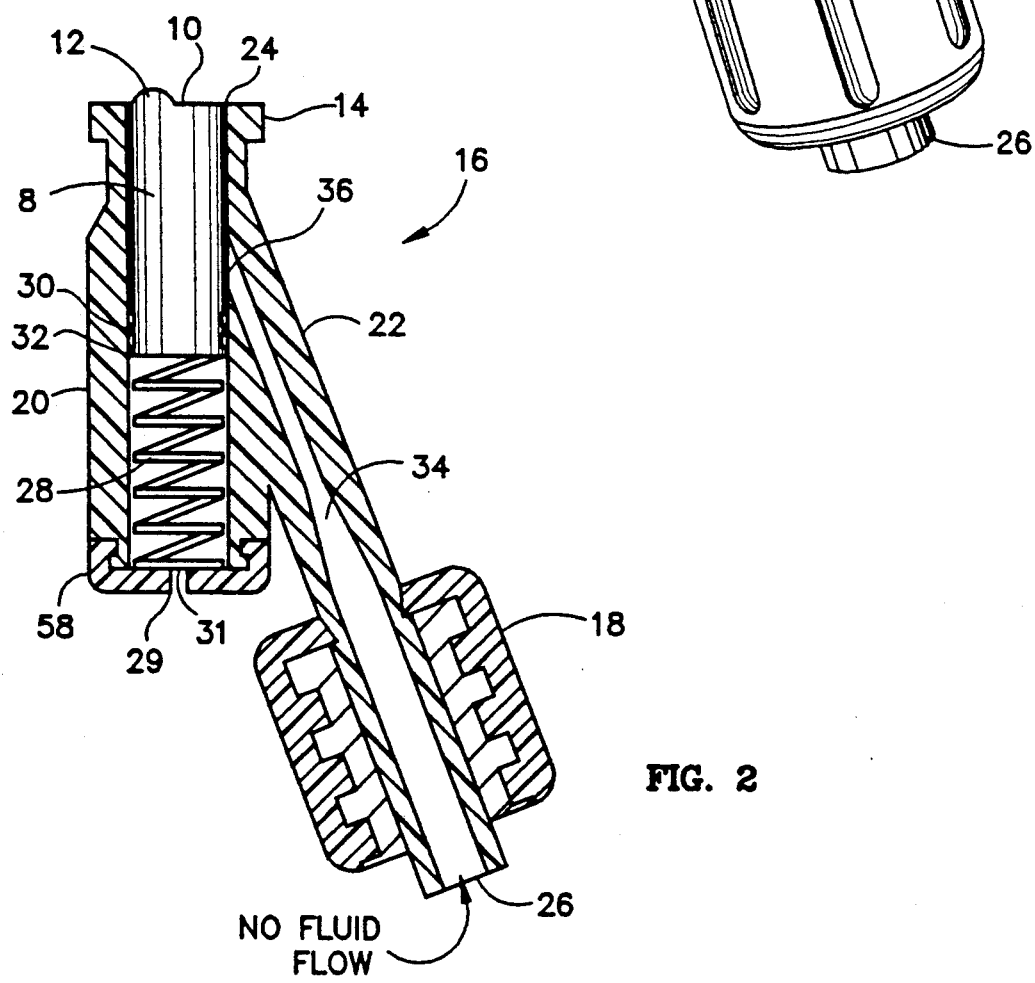
FIG. 2 is a side cut-away view of a variation of the invention showing a piston in the closed position.

FIG. 2 is a side cut-away view of the medical valve assembly 16 showing a piston 8 in the closed position. At the top portion of the valve assembly, there is a piston 8 with a flat surface area 10 and a raised or bump portion 12. This flat surface area 10 rests against an annular sealing lip 24. The piston 8 is biased against the annular sealing ring 24 by biasing spring 28. Biasing pressure from biasing spring 28 in conjunction with the annular sealing ring 24 seals the inner portions of the valve 16 from the atmosphere. The top surface 10 of piston 8 and raised portion 12 of piston 8 along with the annular sealing ring 24 and the top surface of the female luer lock 14 are easily cleaned and do not have any exposed fluid reservoirs. This greatly reduces the possibility of bacteria being introduced into a patient's bloodstream when the medical valve assembly 16 is repeatedly used to administer various medications.

Figure 8A:
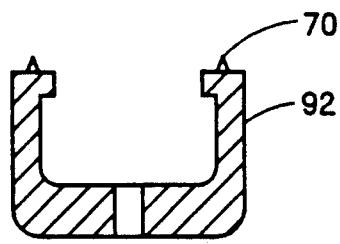
FIGS. 8A through 8D are side views of four various retainer cap configurations used to contain a piston and biasing means in a piston and biasing means housing and FIG. 8E is a top view of FIG. 8D.

The piston 8 is movable inside of the piston and biasing means housing 20 and is lubricated with Dow Corning silicone oil #FS-1265 or other medical grade silicone oil lubricants. Approximately ¼ inch down the length of the piston 8 is a fluid channel inlet 36. When the piston is in the close position the fluid inlet 36 is sealed by the piston and prevents the backflow of fluid from the fluid channel 34 into the interior area of the piston and biasing means housing 20. Fluid from the fluid channel 34 is also prevented from entering into the area occupied by the biasing spring 28 by means of annular sealing rings 30 and 32. The fluid channel housing 22 extends downward to a point where there is a male luer lock 18 which has a fluid outlet 26. In a standard manner, this luer lock connection 18 would be connected to a female luer connector located on a catheter that had been inserted into a patient. When the piston 8 is in the closed position, fluid in the fluid channel 34 is prevented from reaching the outside surface by the position of piston 8 as well as the sealing action between piston 8 and annular sealing ring 24. This feature allows for the maintenance of catheter patency. Piston and biasing means housing 20 has a retaining cap 58 and an air escape hole 29 located at the lower portion of the piston and biasing means housing 20. The air escape hole 29 is sealed with a hydrophobic filter member 31 which allows air to pass in and out of air escape hole 29 but does not allow fluids to pass in. This air escape hole 29 is necessary so that the piston 8 can be moved from the closed to the opened position without encountering too much resistance due to the buildup of air pressure on the interior of housing 20. The piston and biasing means can be inserted through the bottom of housing 20 before the retaining cap 58 is snapped into place and ultrasonically or solvent bonded. FIG. 8A shows an annular energy directing ring 70 that would facilitate ultrasonic bonding of retainer cap 58 to housing 20. Annular energy directing ring 70 would be used in combination with any of the retainer cap embodiments shown in FIGS. 8A through D. Further advantages of the device of the present invention will now be discussed with reference to FIG. 3.

FIG. 3 shows the medical valve assembly 16 as connected to a syringe 40 and a catheter 42. The piston 8 is biased in the opened position by the force of the connection between the female luer lock 14 and the male luer lock connection 44 located at the end of syringe 40. As the male luer lock portion 44 of syringe 40 is connected to the female luer lock portion 14 of the medical valve assembly 16, the outlet end 41 of syringe 40 contacts the raised portion 12 of the piston 8 and causes the piston to be displaced from the closed position and moved downward through the piston and biasing means housing 20 until it is in the opened position as shown in FIG. 3. In this position, the annular sealing ring 24 makes a seal against the outer sidewall 46 of syringe 40. This prevents fluid from entering the interior portion of the male luer lock connector 44.

Figure 7A:
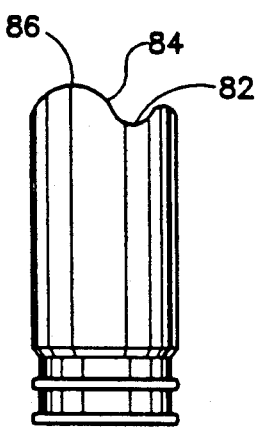
FIGS. 7A and 7B are side views of two piston surface variations and FIGS. 7C through 7F show four syringe tip variations that will work in conjunction with a flat piston surface.
Figure 7B:
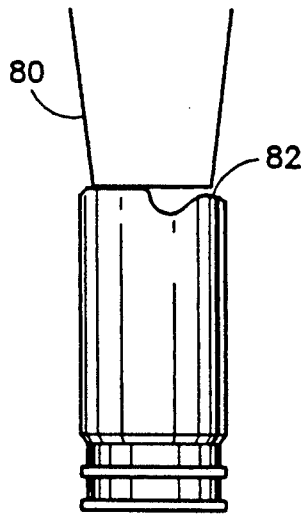
Figure 7C:
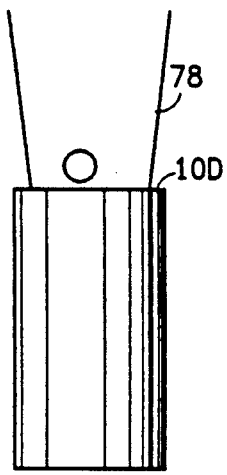
Figure 7D:
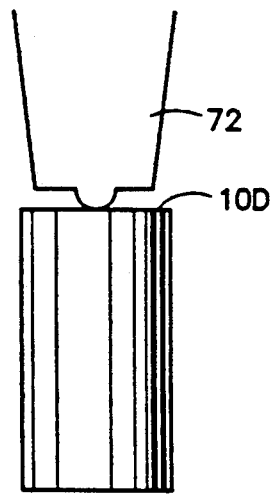
Figure 7E:
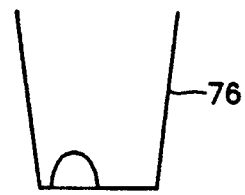
Figure 7F:
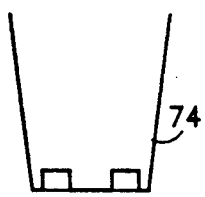

The same type of results can be achieved if the top of piston 8 is completely flat, eliminating raised portion 12, and the end or tip of syringe 40 has a raised portion, bevel, or notch on one section of the outlet end 41 of the syringe 40. FIGS. 7C through 7F show variations of syringe outlet 41 that provide for fluid passage across piston surfaces with or without surface contours. Syringe outlets 72, 74, 76, and 78 all provide acceptable fluid flow. These syringe outlets could also include beveled edges and the like and are defined herein as irregular annular fluid outlets. FIGS. 7A and B show variations of piston surface contours providing fluid flow when used with standard syringe tip 80. The depressed areas 82 shown in FIGS. 7A and 7B provide fluid flow into the fluid channel inlet 36 by allowing fluid under pressure to pass through syringe tip 80 and across the depression area 82. Piston surface 84 incorporates both a bump 86 and a depression 82 to provide similar fluid flow capabilities. These arrangements can achieve the same results as the piston 8 with raised portion 12. However, the arrangement where the raised portion is on the end of the syringe as opposed to the top of piston 8 requires that the correct type of syringe be used. If a flat faced syringe were used then the doctor or nurse administering the medicine would encounter difficulty expelling the fluid from the syringe to the fluid channel 34. Also, the raised portion on the piston is preferred because it has no reservoir or depression that could inhibit efficient cleaning.

Returning to FIG. 3, with the syringe 40 and piston 8 in this position, fluid escapes during the injection process because the raised portion 12 of the piston 8 only contacts a small portion of the annular outlet area 41 of the syringe 40. This allows fluid to escape from the syringe into the fluid channel inlet 36 of fluid channel 34. In a standard manner, pressure generated by the expulsion of fluid from the syringe 40 forces fluid to flow through the fluid channel 34 to the fluid channel outlet 26. This portion of the medical valve assembly 16 has a male luer connector 10 which is then connected to a female luer lock connector 42. Luer lock connector 42 is substantially the same as the female luer lock connection 14 which is part of the top portion of the medical valve assembly 16. In a standard manner, fluid is thus introduced into or removed from a patient.

When the appropriate amount of fluid or medicine has been injected or aspirated, the syringe 40 and male luer lock connection 44 ar disengaged from the female luer lock connection 14. As this process is taking place, and the outlet portion of the syringe 40 is being withdrawn from the piston and biasing means housing 20, the piston 8 is urged into the closed position, as shown in FIG. 2, by biasing spring 28. Air is allowed to pass into the interior of housing 20 through air hole 29 and through membrane 31. The annular sealing rings 30 and 32 and piston 8 wipe the inside wall of piston and biasing means housing 20 to prevent fluid from the syringe 40 and the fluid channel 34 from entering the portion of the housing 20 occupied by the biasing spring 28. As the end portion of syringe 40 is being withdrawn from the piston and biasing means housing 20, the outside diameter of the syringe wall 46 wipes against annular sealing ring 24. In the process of returning the piston 8 to the closed position, the piston 8 seals off the fluid channel inlet 36 to fluid channel 34. This can be seen by comparing the position of piston 8 in FIG. 3 with the position of piston 8 in FIG. 2. During this portion of the sealing process, a small amount of fluid will remain on the surface area 10 of piston 8. When the piston is returned to the closed position as shown in FIG. 2, the top surface of the piston 10 and the raised portion 12 along with the annular sealing ring 24 and the top surface of the female luer lock connector 14 can be easily cleaned due to their surface characteristics. This arrangement does not allow for the creation of an exposed fluid reservoir. Such a reservoir can become an area for the growth of bacteria which could be introduced into the patient's bloodstream upon subsequent use of the device for dispensing medication.

Figure 8B:
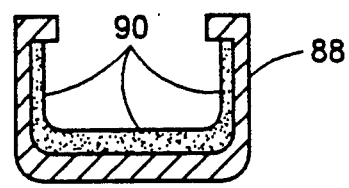
Figure 8C:
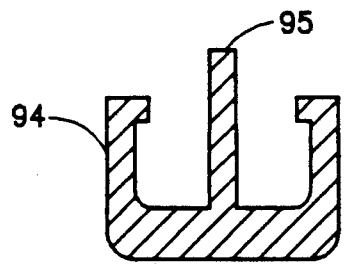
Figure 8D:
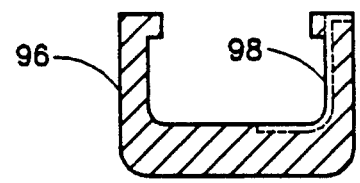
Figure 8E:
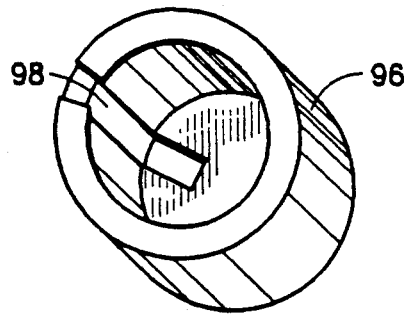

FIG. 4 shows a medical valve assembly in the presently preferred embodiment. In this embodiment the piston and biasing means housing 20 has a retaining cap 58 located on the bottom portion of housing 20. The retaining cap 58 snaps into place when the retaining edges 60 of retaining cap 58 slip into the annular retaining groove 62. The bottom portion of retaining cap 58 has an air escape hole 29 which is sealed with a hydrophobic filter member 31 which is held in place when the retaining cap 58 is snapped and bonded into place. This filter member 31 allows air to pass in and out of the interior portion of housing 20 but does not allow fluids to pass into the inner portion of housing 20. The air escape hole 29 in retainer cap 58 is not required if the volume of area between the piston and retaining cap 58 is large enough so that displacement of the piston to the open position does not significantly increase the pressure in the area behind the piston. The retainer cap 88 in FIG. 8B, illustrates this embodiment and shows that material 90 has been removed from the interior of retainer cap 88, as compared to the retainer cap 92, to provide the required volume of area. In this embodiment, the hydrophobic filter member 31 is not required since there is no air passing into or out of housing 20. FIG. 8C shows a retainer cap 94 which incorporates an integral pin 95 that stabilizes the base of biasing spring 28. Retainer cap 92, FIG. 8A, illustrates a variation in which air escape hole 29 does not incorporate filter member 31 Retainer cap 96, FIGS. 8D and 8E, show air passage 98 directed up the interior wall of the retainer cap body allowing air to escape and return.

Figure 5:
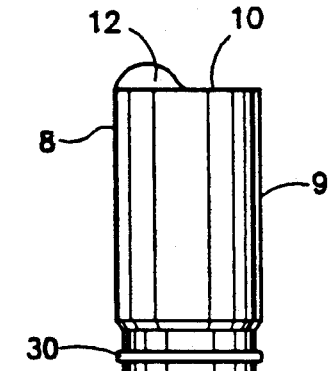
FIG. 5 is a side view of the piston shown in FIGS. 1, 2, and 3.
Figure 6:
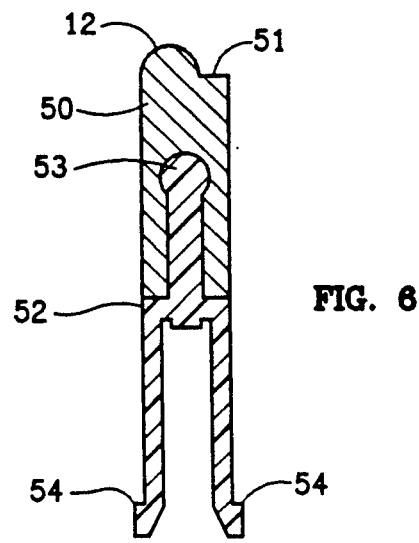
FIG. 6 is a cut-away side view of the preferred piston shown in FIG. 4.

Returning to FIG. 4, on the interior portion of housing 20 is located a piston 50, and a spade 52 having alignment feet 54 which fit into and correspond to alignment channels 56. A biasing means 28, such as a spring, contacts the interior portion of spade 52 and the retaining cap 58 as shown in FIG. 4. The upper portion 53 of spade 52 is located on the interior portion of piston 50. The upper portion 53 of spade 52 fits into the piston 50 to hold it in the interior portion of housing 20, to keep it aligned, and to maintain a flat surface relationship between the flat surface area 51 of piston 50 and the top surface 64 of the female luer lock connector. The two legs 54 at the bottom of spade 52 will slide into alignment slots 56 to hold the piston and spade in place. The dimensions of the piston 50 will be discussed with reference to FIG. 6. The dimensions of piston 50 make it possible to eliminate the annular sealing ring 24 shown in FIGS. 2 and 3. The construction of piston 50 also makes it possible to eliminate the annular sealing rings 30 and 32 shown in FIGS. 2, 3, and 5.

Piston 50 consists of a multi-diameter shape of approximately 0.450 inches in length. There is approximately 0.005 to 0.008 inches compression fit with the interior of the housing 20 for a distance of approximately 0.050 inches on each end of the piston which provides the sealing required to prevent leaks and enable easy wiping of piston surface 51 when in the closed position. Between the larger diameters on each end of piston 50, the diameter of the piston will range from a minimum of 0.001 to 0.003 inches smaller than the piston housing 20 diameter.

The operation of this device is similar to the device described in FIGS. 2 and 3. When the piston 50 is in the closed position, as shown in FIG. 4, the piston 50 seals the fluid channel 34 from the outside atmosphere. When the piston 50 is in the opened position, fluid passes from the syringe to the fluid channel as previously described with reference to FIG. 3. In lieu of the annular sealing lip 24 in FIGS. 2 and 3, sealing of the outer sidewall of the syringe 40 to the biasing means housing 20 is accomplished through an inverse taper relationship between the inside diameter of housing 20 and the outside diameter of the fluid outlet of the syringe. This results in a friction fit seal of the luer connectors. The inner walls of housing 20 are multi-diameter, starting at 0.167 inches at top to provide an industry standard female luer taper for ¼ to ½ of the distance to the fluid channel inlet 36. Further down, the inner walls of housing 20 have a one to three percent minimum draft as required by injection molding techniques. The piston 50 to the housing 20 sealing requirements of 0.005 to 0.008 inches piston compression is also taken into account in specifying the minimum draft. When a syringe is removed, the piston returns to the closed position due to the biasing force of biasing means 28. As the piston is returning to the closed position, air is drawn into the interior of housing 20 through air hole 29. The air passes through the filter membrane 31 which does not allow water or other fluids and contaminants to pass into the interior of housing 20 as described with reference to FIG. 3. FIG. 4 shows the output end of the valve assembly with a male luer lock connector 18 but not show the threads of male luer lock connector.

The advantages of this device include the alignment and retaining features provided by the arrangement of spade 52 and piston 50. The alignment legs 54 of the spade 52 keep the raised portion 12 of piston 50 in the correct position and also prevent the piston 50 from coming out of the top of housing 20. This arrangement also facilitates manufacturing in that the piston 50, the spade 52, the biasing means 28 are all inserted through the bottom of housing 20 and then are retained in place when retaining cap 58 is snapped and bonded into place.

As shown from the previous description, the advantages of this device, in its operation, are that it can be used repeatedly without the use of a needle to introduce medications into, or aspirate fluids from, a patient's bloodstream. The other major advantage of this arrangement is the easily cleanable top surface of the female luer lock connector 14 and the easily cleanable top surface 10 of piston 8. This ability to be easily cleaned along with the absence of an exposed fluid reservoir greatly reduces the possibility of bacterial infection by repeated use of the medical valve assembly 16.

Figure 9:
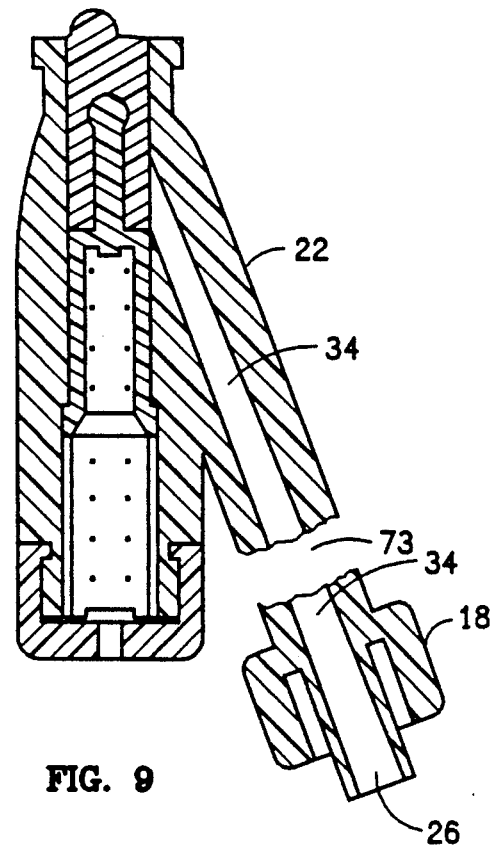
FIG. 9 shows a side cut-away view of a valve assembly that can be manufactured by injection molding and that can be fitted with different fluid outlet configurations.

In FIG. 9, the fluid channel outlet 26 and the bottom ¼ to ½ of the fluid channel 34 are molded as a separate component to allow for injection molding requirements. The bottom portion of the fluid channel 34 and outlet 26 are then ultrasonically or solvent bonded to the upper portion of the fluid channel housing 22. This also facilitates the attachment of other types of fittings and devices, such as the male luer slip connector, to the present invention in a standard or custom manner.

Other aspects and advantages of the present invention will now be discussed. This medical valve assembly 16 can be used with catheters, I.V. sets or any other device using a luer lock or luer slip fitting. The absence of needles from this device prevents the potential for a "needle stick" which is a major cause for concern due to the AIDS virus. The biasing means 28 must have enough restoring force to return the top portion of the piston 8 to the flush or sealed position. When the piston is in the open position, the valve should allow a flow rate at least equal to that achieved with an 18 gauge needle. When the piston is in the opened position, and a syringe is inserted into the interior portion of piston and biasing means housing, an effective seal must be generated between the inverse luer taper and the outer wall of the syringe.

The materials used for manufacturing the medical valve assembly should have the characteristics of a currently acceptable medical grade plastic that can be precision molded and maintain its dimensions under normal hospital conditions. The inner wall of piston and biasing means housing 20 should be rigid and allow for a secure fit between the outer surface of piston 8 and the inner wall of housing 20. The material should be resistant to alcohol and have a low coefficient of friction. Examples of such materials include polycarbonate, PVC, nylon, delrin, and hydrel. The preferred embodiment uses polycarbonate because it is commonly used in components that would be attached to the present device, it can be sterilized, it has a long shelf life, and it can be used in a clear, translucent, or colored form.

The piston 8 should be of a currently acceptable medical grade plastic which can be precision molded and maintain its dimensions under normal conditions. The material should be adaptable so that a series of thin flexible annular wiping/sealing rings 30 and 32 (FIG. 5) can be fabricated and can maintain their ability to seal the biasing spring 28 from fluid introduced into the fluid channel 34. In the preferred embodiment shown in FIG. 4, the piston should be compressible, as previously described, resistant to alcohol, and should be a material or combination of materials that, in combination with the housing 20 material, will provide a low coefficient of friction and lend itself to a medical grade silicone oil lubricant coating. Examples of such materials for the piston 8 include nylon, delrin, hydrel, polyurethane, silicone, or other thermoplastic elastomeric materials. The presently preferred material is silicone such as Dow Corning 4765.

The biasing means should be a plastic or metal spring, a high viscosity silicone, air, or a combination of any of these. Elastomeric materials including cellular, noncellular, synthetic rubbers and plastics, such as highly dense or closed polyurethane, styrene butadenes, or isoprenes should suffice. These materials are disclosed in U.S. Pat. No. 4,324,239, hereby incorporated by this reference. The spade should be a thermoplastic material such as polycarbonate PVC, polypropylene, nylon or delrin. Polypropylene is presently preferred because it is easily moldable, cost effective, and can be radiation sterilized.

While the device of the present invention is shown with reference to the FIGS. 1 through 9, the instant invention is not to be limited to the exact details of construction shown and described herein, for obvious modifications can be made by a person skilled in the art.

What is claimed is:

1. A valve assembly adapted to facilitate the administration and withdrawal of fluid from a patient comprising valve assembly housing having an input side and an output side, a fluid channel having an input opening, a piston and biasing means housing wherein said fluid channel extends between the output side of said valve assembly housing and said piston and biasing means housing, said input opening of said fluid channel is connected to said piston and biasing means housing, piston means located in said piston and biasing means housing, said piston means being movable between an open and closed position, said piston means sealing the input opening of said fluid channel from said input side of said valve assembly housing when said piston means is in said closed position, said piston means having a top surface forming a part of said valve assembly housing input side, said top surface being flat except for at least one raised portion, said raised portion being adapted to contact the output end of a syringe, said piston means is adapted to be displaced into said open position when a syringe is connected to the input side of said valve assembly housing, thereby permitting fluid connection between said output end of said syringe and the input opening of said fluid channel, the input side of said valve assembly housing having a sealing means for forming a seal between said input side of said valve assembly housing and said output end of said syringe, and biasing means located in said piston and biasing means housing for biasing said piston means in said closed position.

2. A valve assembly as in claim 1 wherein
   said input side of said valve assembly housing is a female luer lock connector and said output side of said valve assembly housing is a male luer lock connector.

3. A valve assembly as in claim 1 wherein said piston means having at least one depression area with respect to said top surface.

4. A valve assembly as in claim 1 wherein
   said biasing means is a spring.

5. A valve assembly as in claim 1 wherein
   said piston and biasing means housing has alignment channels and said piston means including a spade having alignment feet, said alignment feet are adapted to fit into said alignment channels.

6. A valve assembly adapted to facilitate the administration and withdrawal of fluid from a patient comprising valve assembly housing having an input side and an output side, a fluid channel having an input opening, a piston and biasing means housing wherein said fluid channel extends between the output side of said valve assembly housing and said piston and biasing means housing, said input opening of said fluid channel is connected to said piston and biasing means housing, piston means located in said piston and biasing means housing, said piston means being movable between an open and closed position, said piston means sealing the input opening of said fluid channel from said input side of said valve assembly housing when said piston means is in said closed position, said piston means having a top surface forming a part of said valve assembly housing input side, said top surface being flat except for at least one raised portion, said raised portion being adapted to contact the output end of a syringe, said piston means is adapted to be displaced into said open position when a syringe is connected to the input side of said valve assembly housing, thereby permitting fluid connection between said output end of said syringe and the input opening of said fluid channel, and biasing means located in said piston and biasing means housing for biasing said piston means in said closed position.

7. A valve assembly as in claim 6 wherein said input side is a female luer lock connector and said output side is a male luer lock connector.

8. A valve assembly as in claim 6 wherein
   said piston means having at least one depressed area with respect to said top surface of said piston means.

9. A valve assembly as in claim 6 wherein
   said biasing means is a spring.

10. A valve assembly as in claim 6 wherein said piston and biasing means housing having alignment channels and said piston means having a spade with alignment feet that fit into said alignment channels for guiding said piston means from the closed to the open position.

11. A valve assembly adapted to facilitate the administration and withdrawal of fluid from a patient comprising valve assembly housing having an input side and an output side, a fluid channel having an input opening, a piston and biasing means housing wherein said fluid channel extends between the output side of said valve assembly housing and said piston and biasing means housing, said input opening of said fluid channel is connected to said piston and biasing means housing, piston means located in said piston and biasing means housing, said piston means being movable between an open and closed position, said piston means sealing the input opening of said fluid channel from said input side of said valve assembly housing when said piston means is in said closed position, said piston means having a top surface forming a part of said valve assembly housing input side, said top surface being flat except for at least one depressed portion, said top surface being adapted to contact the output end of a syringe, said piston means is adapted to be displaced into said open position when a syringe is connected to the input side of said valve assembly housing, thereby permitting fluid connection through said depressed portion and between said output end of said syringe and the input opening of said fluid channel, and biasing means located in said piston and biasing means housing for biasing said piston means in said closed position.

12. A valve assembly as in claim 11 wherein said input side is a female luer lock connector and said output side is a male luer lock connector.

13. A valve assembly as in claim 11 wherein said biasing means is a spring.

14. A valve assembly as in claim 11 wherein said piston and biasing means housing has alignment channels and said piston means including a spade having alignment feet that fit into said alignment channels for guiding said piston from the closed to the open position and from the open to the closed position.

15. A valve assembly adapted to facilitate the administration and withdrawal of fluid from a patient comprising valve assembly housing having an input side and an output side, a fluid channel having an input opening, a piston and biasing means housing wherein said fluid channel extends between the output side of said valve assembly housing and said piston and biasing means housing, said input opening of said fluid channel is connected to said piston and biasing means housing, piston means located in said piston and biasing means housing, said piston means being movable between an open and closed position, said piston means sealing the input opening of said fluid channel from said input side of said valve assembly housing when said piston means is in said closed position, said piston means having a top surface forming a part of said valve assembly housing input side, said top surface being flat, said top surface being adapted to contact the outlet end of a syringe having an irregular annular fluid outlet, said piston means is adapted to be displaced into said open position when a syringe is connected to the input side of said valve assembly housing, thereby permitting fluid connection between said output end of said syringe and the input opening of said fluid channel, and biasing means located in said piston and biasing means housing for biasing said piston means in said closed position.

16. A valve assembly as in claim 15 wherein said input side is a female luer lock connector and said output side is a male luer lock connector.

17. A valve assembly as in claim 15 wherein said biasing means is a spring.

18. A valve assembly as in claim 15 wherein said piston and biasing means housing having alignment channels and said piston means having a spade and alignment feet, said alignment feet fitting into said alignment channels and guiding said piston means from the closed to the open position.

* * * * *